United States Patent [19]

Nakajima et al.

[11] Patent Number: 5,214,151
[45] Date of Patent: May 25, 1993

[54] METHOD FOR THE PREPARATION OF α, β-UNSATURATED KETONES

[75] Inventors: Masashi Nakajima; Tadashi Kyotani; Keiichi Tsukashima, all of Takaoka, Japan

[73] Assignee: Nippon Soda Co., Ltd., Tokyo, Japan

[21] Appl. No.: 730,843
[22] PCT Filed: Nov. 15, 1990
[86] PCT No.: PCT/JP90/01488
§ 371 Date: Jul. 15, 1991
§ 102(e) Date: Jul. 15, 1991
[87] PCT Pub. No.: WO91/07371
PCT Pub. Date: May 30, 1991

[30] Foreign Application Priority Data

Nov. 17, 1989 [JP] Japan .................... 297388

[51] Int. Cl.$^5$ .................... C07D 213/50; C07C 45/72; C07C 49/217
[52] U.S. Cl. .................... 546/340; 564/305; 568/313
[58] Field of Search .................... 568/313; 546/340; 564/305

[56] References Cited

U.S. PATENT DOCUMENTS 4,945,184  7/1990  Pugach et al. .................... 568/313

OTHER PUBLICATIONS

Chem. Abstract: U.S.S.R. from: Otkrytiya, Izobret. 1985(32), 242 Kaku Tsutomu et al. Nippon Soda Co., Ltd.

Derwent Abstract: U.S.S.R. from: Otkrytiya, Izobret, 1985(32), 242 Kaku Tsutomu, et al. Nippon Soda Co., Ltd.

Primary Examiner—C. Warren Ivy
Assistant Examiner—D. Margaret M. Mach
Attorney, Agent, or Firm—Joseph C. Mason, Jr.; Ronald E. Smith

[57] ABSTRACT

The present invention relates to a method for the preparation of α, β-unsaturated ketones represented by general formula (II)

$$RCH=CHCCH_3 \underset{O}{\overset{\parallel}{}} \quad (II)$$

(where R is a heterocyclic group with nitrogen atom in the ring or a phenyl group with electron donative substituents) which comprises reacting aldehydes represented by general formula (I)

$$RCHO \quad (I)$$

(where R is a s defined above) with acetone, in the presence as a catalyst of one or tow or more compounds selected from the group consisting of perhydroisoindole and pyrrolidine which may have substituents, in a water solvent, at 20° C. to 40° C., and then reacting at the reflux temperature.

The compound (II) is extremely important as an intermediate for pharmaceuticals and agricultural chemicals.

6 Claims, No Drawings

METHOD FOR THE PREPARATION OF α,β-UNSATURATED KETONES

FIELD OF INVENTION

This invention relates to a method for the preparation of α,β-unsaturated ketones represented by general formula (II)

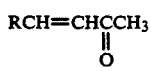

$$RCH=CHCCH_3 \quad (II)$$
$$\parallel$$
$$O$$

where R is a heterocyclic group with nitrogen atom in the ring or a phenyl group with electron donative substituents (hereinafter referred to as Compound II), Compound (II) is extremely important as an intermediate for pharmaceuticals and agricultural chemicals.

DESCRIPTION OF RELATED ART

Conventionally known methods for the preparation of Compound II include a synthetic method by aldol condensation of aldehyde and acetone [described in such documents as Ber. 35 3569 (1902)] and a method that aldehyde and acetoacetate are Knovenagel condensed, hydrolyzed and decarboxylated [described in such documents as J. Org. Chem. 22 1451 (1957)]. The methods are not applicable to industrial manufacturing since the yield is generally low.

An object of this invention is to provide methods for the preparation of α,β-unsaturated ketones which are excellent as industrial manufacturing methods.

SUMMARY OF THE INVENTION

The inventors carried out various studies to accomplish the above purposes, and found that Compound (II) can be obtained with good yield by reacting specific aldehydes with acetone, in a water solvent, using specific catalysts, while heating, and thus have accomplished this invention.

That is, this invention is a method for the preparation of α,β-unsaturated ketones represented by general formula (II)

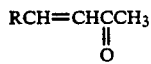

$$RCH=CHCCH_3 \quad (II)$$
$$\parallel$$
$$O$$

where R is a heterocyclic group with nitrogen atom in the ring or a phenyl group with electron donative substituents which comprises reacting aldehydes represented by general formula (I)

$$RCHO \quad (I)$$

(where R is as defined above) with acetone, in the presence as a catalyst of one or two or more compounds selected from the group consisting of perhydroisoindole and pyrrolidine which may have substituents, in a water solvent, at 20° C. to 40° C., and then reacting at the reflux temperature.

Aldehydes represented by general formula (I)

$$RCHO \quad (I)$$

(where R is as defined above) (hereinafter referred to as Compound I) and used in this invention include benzaldehydes with electron donative substituents such as p-(N,N-dimethylamino) benzaldehyde and 2,4,6-trimethylbenzaldehyde; and heterocyclic aldehydes with nitrogen atom in the ring such as 2-pyridine carbaldehyde, 3-pyridine carbaldehyde and 4-pyridine carbaldehyde.

Compounds used as catalyst include perhydroisoindole and pyrrolidine represented by the following formula which may be substituted;

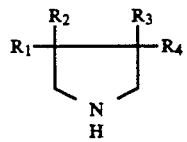

where $R_1$, $R_2$, $R_3$ and $R_4$ are hydrogen or lower aliphatic groups.

Their concrete examples are pyrrolidine and pyrrolidines substituted at the 3 and/or 4 positions such as 3-methylpyrrolidine, 3-ethylpyrrolidine, 3,3-dimethylpyrrolidine, 3,3-diethylpyrrolidine, 3,4-dimethylpyrrolidine and 3,4-diethylpyrrolidine.

Two or more of these catalysts can be used by mixing. Water is indispensable as a catalyst. A reaction in an organic solvent results in extremely low yield.

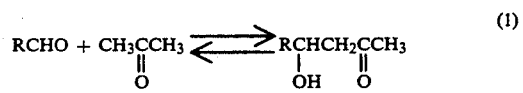

$$RCHO + CH_3CCH_3 \rightleftharpoons RCHCH_2CCH_3 \quad (1)$$
$$\qquad \parallel \qquad\qquad\quad | \quad \parallel$$
$$\qquad O \qquad\qquad\quad OH \quad O$$

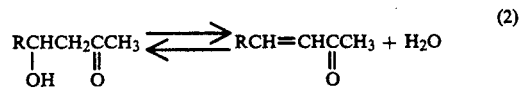

$$RCHCH_2CCH_3 \rightleftharpoons RCH=CHCCH_3 + H_2O \quad (2)$$
$$| \quad \parallel \qquad\qquad\qquad \parallel$$
$$OH \quad O \qquad\qquad\qquad O$$

The reaction proceeds according to the above reaction equations (1) and (2). If R is a heterocyclic group containing N in the ring such as pyridyl group, Reaction (2) proceeds more, and α,β-unsaturated ketones are formed from β-hydroxyketones during the addition reaction or post treatment. Therefore, it is difficult to isolate β-hydroxyketones. α,β-unsaturated ketones may be formed by addition reaction at room temperature followed by dehydration with strong acid. However it is rather preferable to convert from β-hydroxyketones to α,β-unsaturated ketones by heating during the addition reaction.

If R is a phenyl group with electron donative substituents such as N-dimethylamino group or trimethyl group, the equilibrium of (1) shifts to the aldehyde side, and the reaction does not proceed. Therefore Reaction (2) is advanced by heating and the equilibrium is shifted to synthesize α,β-unsaturated ketones.

A way of implementing the preparation method for Compound I is described in detail in the following;

1.5 to 20 times moles, preferably 3 to 10 times moles, to a mole of Compound I, of acetone; 50 to 2000 ml, preferably 200 to 500 ml, to a mole of Compound I, of water; and 0.002 to 0.1 moles, preferably 0.01 to 0.05 moles, to a mole of Compound I, of catalyst are mixed. Into the resulting mixture is dropped a mole of Compound I at 20° to 40° C. over 0.5 to 5 hours, then the mixture is kept stirring under reflux for 0.5 to 7 hours.

After the reaction is completed, the reaction solution is neutralized with acid such as hydrochloric acid to pH 1 to 6, acetone is distilled and recovered. Then the residue is extracted with water-insoluble organic solvent such as chloroform or toluene. The extract is concentrated and distilled under vacuum to give the intended Compound I.

DESCRIPTION OF THE PREFERRED EMBODIMENTS

This invention is further described in detail by reference to the following examples. The range of this invention is not limited at all by the following examples.

EXAMPLE 1

Into a reaction vessel of 1 l in inside volume were placed 290.5 g (5 moles) of acetone, 300 ml of water and 3.6 g (0.05 moles) of pyrrolidine, to which 149.2 g (1 mole) of p-(N,N-dimethylamino) benzaldehyde was dropped over an hour while keeping at 30° C. Then the resulting solution was stirred under reflux for 9 hours.

The solution was neutralized with concentrated hydrochloric acid up to pH 4.5, and heated to distill up to the distillation temperature of 100° C. Then 300 ml of chloroform was added, and the solution was neutralized with 28% NaOH aqueous solution to pH 12 and separated.

Furthermore, the aqueous layer was extracted with 200 ml of chloroform twice. The obtained chloroform layers were combined to the previous chloroform layer to concentrate. The obtained crystal was recrystallized from a mixture solvent of benzene and hexane to give 113.6 g (crude yield: 60.0%) of yellow crystal with melting point of 137.5° to 140.5° C.

The crystal was analyzed by gas chromatography to find that the intended product, 4-[p-(N,N-dimethylamino) phenyl]-3-butene-2-one, was 97.8% in purity. (Yield: 58.7% to p-(N,N-dimethylamino) benzaldehyde)

EXAMPLE 2

Into a reaction vessel of 300 ml in inside volume were placed 87.2 g (1.5 moles) of acetone, 90 ml of water and 2.0 g (0.02 moles) of 3,3-dimethylpyrrolidine, to which 29.6 g (0.2 mole) of 2,4,6-trimethylbenzaldehyde was dropped over an hour while keeping at 30° C. Then the resulting solution was stirred under reflux for 7 hours.

The solution was adjusted the pH to 4.5 with concentrated hydrochloric acid, and heated to distill up to the distillation temperature of 100° C. Then 80 ml of chloroform was added to the resulting solution to extract and the solution was separated. The toluene layer was concentrated. The obtained extract was distilled under reduced pressure to give distillate with boiling point of 94° to 96° C. at 0.02 mmHg. This distillate crystallized after the distillation to give 27.1 g of yellow crystal with boiling point of 64° to 69° C. (crude yield: 72.0%).

The crystal was analyzed by gas chromatography to find that the intended product, 4-(2,4,6-trimethylphenyl)-3-butene-2-one, was 94.8% in purity. (Yield: 68.3% to 2,4,6-trimethylbenzaldehyde)

EXAMPLE 3

Into a reaction vessel of 1 l in inside volume were placed 290.5 g (5 moles) of acetone, 300 ml of water and 3.6 g (0.05 moles) of pyrrolidine, to which 107.1 g (1 mole) of 3-pyridine carbaldehyde was dropped over an hour while keeping at 30° C. Then the resulting solution was stirred under reflux for 8 hours.

After the reaction was completed, concentrated hydrochloric acid was dropped to make the pH 4.5, and the solution was heated to distill up to the distillation temperature of 100° C. Then 300 ml of chloroform was added, and the solution was neutralized with 28% NaOH aqueous solution to pH 12 and separated. Furthermore, the aqueous layer was extracted with 200 ml of chloroform twice.

The obtained chloroform layers were combined to the previous chloroform layer to concentrate. The obtained extract was distilled under reduced pressure to give 122.8 g (crude yield: 83.4%) of yellow extract with boiling point of 113° C. at 1.1 mmHg and $n_D^{18} 1.5941$.

The extract was analyzed by gas chromatography to find that the intended product, 4-(3-pyridyl)-3-butene-2-one, was 94.9% in purity. (Yield: 79.1% to 3-pyridine carbaldehyde)

INDUSTRIAL APPLICABILITY

This invention is to provide methods for the preparation of α, β-unsaturated ketones having heterocyclic groups with nitrogen atom in the ring or phenyl groups with electron donative substituents, which are difficult to synthesize, from corresponding aldehydes andacetone, with good yield. The invention is greatly significant in industry.

We claim:

1. Method for preparing an α, β-unsaturated ketone which comprises
   (a) admixting acetone, water and a catalyst comprising perhydroisoindole or pyrrolidine which is optionally substituted or mixtures thereof;
   (b) adding to the admixture an aldehyde of the formula I

R—CHO         (I)

wherein R is (i) a heterocyclic group with a nitrogen atom in the ring or (ii) a phenyl group with electron donative substitutes while maintaining the temperature of the admixture and aldehyde from 20° C. to 40° C.;
   (c) raising the temperature of the admixture and aldehyde from 20° C. to 40° C. by subjecting the admixture and aldehyde to reflux conditions;
   (d) maintaining such reflux conditions for a time sufficient to thereby produce α, β-unsaturated ketone of the formula II

RCH=CHCCH₃         (II)
      ‖
      O wherein R has the above mentioned meaning; with the following provision: β-hydroxyketone is not isolated.

2. Method according to claim 1 wherein the heterocyclic group is pyridyl.

3. Method according to claim 1 wherein the electron donative substituent is N-dimethylamino.

4. Method according to claim 1 wherein the electron donative substituent is trimethyl.

5. Method according to claim 1 wherein the admixture comprises
   (a) 1.5 to 20 moles of acetone,
   (b) 200 to 500 ml of water,
   (c) 0.002 to 0.1 moles of catalyst, to which is added
   (d) one (1) mole of aldehyde.

6. Method for preparing an α, β-unsaturated ketone which comprises
   (a) admixing acetone, water and a catalyst compound selected from the group consisting of perhydroisoindole, pyrrolidine optionally substituted, and mixtures thereof;

(b) adding to the admixture an aldehyde selected from the group consisting of p-(N,N-dimethylamino) benzaldehyde; 2,4,6trimethylbenzaldehyde; 2-pyridine carbaldehyde, 3-pyridine carbaldehyde and 4-pyridine carbaldehyde while maintaining the admixture and aldehyde at a temperature from 20° C. to 40° C.

(c) raising the temperature of the admixture and aldehyde to reflux temperature for a time sufficient to thereby produce $\alpha,\beta$-unsaturated ketone, without isolating any intermediate $\beta$-hydroxyketone, comprising 4-[p-(N,N-dimethylamino phenyl]-3-butene-2-one, 4-(2,4,6-trimethylphenyl)-3-butene-2-one, 4-(3-pyridyl)-3-butene-2-one, or 4-(4-pyridyl)-3-butene-2-one.

* * * * *